US 7,846,660 B1

(12) United States Patent
Albert et al.

(10) Patent No.: US 7,846,660 B1
(45) Date of Patent: Dec. 7, 2010

(54) MICROARRAYS HAVING MULTIPLE OLIGONUCLEOTIDES IN SINGLE ARRAY FEATURES

(75) Inventors: Thomas Albert, Madison, WI (US); Jason Norton, Madison, WI (US); Roland Green, Madison, WI (US)

(73) Assignee: Roche Nimblegen, Inc., Wilmington, DE (US)

(*) Notice: Subject to any disclaimer, the term of this patent is extended or adjusted under 35 U.S.C. 154(b) by 318 days.

(21) Appl. No.: 11/604,582

(22) Filed: Nov. 27, 2006

Related U.S. Application Data

(62) Division of application No. 10/674,766, filed on Sep. 30, 2003, now abandoned.

(60) Provisional application No. 60/415,046, filed on Oct. 1, 2002.

(51) Int. Cl.
 *C12Q 1/68* (2006.01)
 *C12M 1/34* (2006.01)
 *C07H 21/00* (2006.01)

(52) U.S. Cl. ............... 435/6; 435/287.2; 536/23.1; 536/25.3; 536/25.31

(58) Field of Classification Search ............ 435/6, 435/287.2; 536/23.1, 25.3, 25.31
See application file for complete search history.

(56) References Cited

U.S. PATENT DOCUMENTS 5,959,098 A    9/1999    Goldberg et al.

6,426,184 B1 *   7/2002   Gao et al. .................. 435/6

FOREIGN PATENT DOCUMENTS

WO   WO 9509248 A1   4/1995
WO   WO00/11223   *  3/2000

OTHER PUBLICATIONS

Beier et al, Synthesis of photolabile 5'-O-phosparamidites for photolithographic production of microarrays of inversely oriented oligonucleotides, 2001, Helvetic Chimica Acta, 84, 2089-2095.*
Albert et al., "Light-directed 5'—3' synthesis of complex oligonucleotide microarray." Nucleic Acids Research, 31:e35, 2003.

* cited by examiner

*Primary Examiner*—Stephen Kapushoc
*Assistant Examiner*—Narayan K Bhat
(74) *Attorney, Agent, or Firm*—Quarles & Brady LLP

(57) ABSTRACT

The present invention is a method for synthesizing microarrays having different oligonucleotides present within one feature area of the array. The method utilizes the techniques common to microarray synthesis, but limits the duration in which selected feature areas on the array are initially dosed with light so as to only deprotect a calculated ratio of the compounds forming the array's binding layer. The compounds initially deprotected are capped with a non-photosensitive protecting group, such as di-methoxy-trityl, to inhibit their involvement in the synthesis of a first group of DNA strands built onto the array. Once the first group of DNA strands have been synthesized, the original deprotected group may then be further processed to build one or more groups of DNA strands in the same feature area as the first group of DNA strands. The present invention also includes microarrays manufactured using the method.

6 Claims, 2 Drawing Sheets

MICROARRAYS HAVING MULTIPLE OLIGONUCLEOTIDES IN SINGLE ARRAY FEATURES

CROSS-REFERENCE TO RELATED APPLICATIONS

This application is a divisional of U.S. application Ser. No. 10/674,766, filed Sep. 30, 2003 now abandoned, which claims priority from U.S. provisional patent application Ser. No. 60/415,046 filed Oct. 1, 2002, each is incorporated herein by reference in its entirety.

STATEMENT REGARDING FEDERALLY SPONSORED RESEARCH OR DEVELOPMENT

Not applicable.

BACKGROUND OF THE INVENTION

The advent of DNA microarray technology makes it possible to build an array of hundreds of thousands of DNA sequences in a very small area, such as the size of a microscopic slide. See, e.g., U.S. Pat. No. 6,375,903 and U.S. Pat. No. 5,143,854, each of which is hereby incorporated by reference in its entirety. The disclosure of U.S. Pat. No. 6,375,903 enables the construction of so-called maskless array synthesizer (MAS) instruments in which light is used to direct synthesis of the DNA sequences, the light direction being performed using a digital micromirror device (DMD). Using an MAS instrument, the selection of DNA sequences to be constructed in the microarray is under software control so that individually customized arrays can be built to order. In general, MAS based DNA microarray synthesis technology allows for the parallel synthesis of over 800,000 unique oligonucleotides in a very small area of a standard microscope slide. The microarrays are generally synthesized by using light to direct the addition of single nucleotides to the oligonucleotides under construction at specific locations on an array, these locations being called features. Typically, the objective is to synthesize many identical oligonucleotides, each having the same nucleotide sequence, in each feature of the array, i.e. there are multiple probes in each feature, but all those probes have the same nucleotide sequence. For certain applications it would be advantageous to have oligonucleotides of different sequences present within one feature of the array, and be able to control the ratio and direction (5'-3', or 3'-5') of these oligonucleotides.

BRIEF SUMMARY OF THE INVENTION

The present invention is summarized as a method for synthesizing a microarray having oligonucleotides of different sequences present within one feature of the array. The present invention also includes a method for synthesizing a microarray to control the ratio and direction (5'-3', or 3'-5') of the oligonucleotides. The present invention also includes microarrays manufactured using the disclosed methods.

The method utilizes the techniques common to microarray synthesis, but limits the duration in which selected feature areas on the array are initially dosed with light so as to only deprotect a calculated ratio of the compounds forming the array's binding layer. The compounds initially deprotected are capped with a non-photosensitive protecting group, such as di-methoxy-trityl, to inhibit their involvement in the synthesis of the first group of DNA strands built onto the array. Once the first group of DNA strands have been synthesized, the original deprotected group may then be further processed to build a second group of DNA strands in the same feature area as the first group of DNA strands. The same concept may also be employed to build additional groups of DNA strands in order to provide feature areas containing more than two different groups of DNA strands. The DNA strands can be constructed 5' to 3' or 3' to 5', depending solely on the orientation of the photo-labile conjugated nucleosides used in the process.

Other objects, advantages and features of the present invention will become apparent from the following specification and drawings.

DETAILED DESCRIPTION OF THE INVENTION

Figure 1:
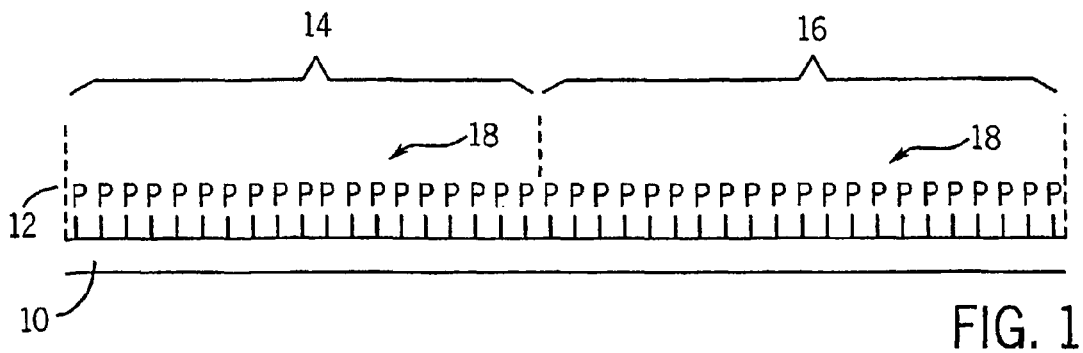
FIGS. 1 to 4 are an schematic illustration process of microarray synthesis including two oligonucleotides synthesized in the same feature area.

The present invention provides a method for synthesizing a microarray having a number of features and in which one or more features can have multiple probes of different sequences present within them. The method contemplates that two or more probes or oligonucleotides can be constructed in single features of the microarray, and further provides a method for controlling the ratio of the relative numbers of the two probes in the feature. The method also permits the direction (5'-3', or 3'-5') of these oligonucleotides to be controlled so that each of the two oligonucleotides in a single feature can be in the same direction or they can be in opposite directions.

It is an advantage of the methods described here that they use the techniques common to microarray synthesis, but uses modifications of those method to achieve new products. For example, the method makes use of the now well-understood process of using light directed de-protection to select areas on the microarray for a de-protection step, but limits the duration in which selected feature areas on the array are initially dosed with light so as to only de-protect not entire features, but only a calculated portion of the area of each feature. The area of the array thus de-protected is then capped with a non-photosensitive protecting group to inhibit the participation of those areas in the synthesis of the first group of oligonucleotides built onto the feature of the array. Once the first group of oligonucleotides have been synthesized, the original de-protected and capped area may then be de-capped. This can be done by making the protecting cap be acid or base labile, and introducing an acid or base into the microarray to de-cap the capped areas. Then, after restoring appropriate pH, the nucleotide addition process can be re-started to synthesize a second group of oligonucleotides in the same feature area as the first group of oligonucleotides. The same concept may also be employed to build additional groups of DNA strands in order to provide feature areas containing more than two different groups of DNA strands.

For the purpose of this invention, the term feature is used for an area on the array that has been intended in prior art microarrays to have the same nucleotide probe or probes throughout its area. In the past, microarrays have had features in which the feature contains only probes or oligonucleotides of the same nucleotide sequence. This is the first known instance in which it has been proposed or enabled to put probes of two or more different sequences in the same feature of a microarray. So for the purposes of this invention, a feature means a portion of a microarray in which two or more probes are synthesized in the same general physical region of the microarray, a region that is preferable distinct from the region in which other probes are constructed.

The terms probe and oligonucleotides are used interchangeably here to refer to the molecules of single stranded DNA (or RNA) which are synthesized on the microarray.

Figure 2:
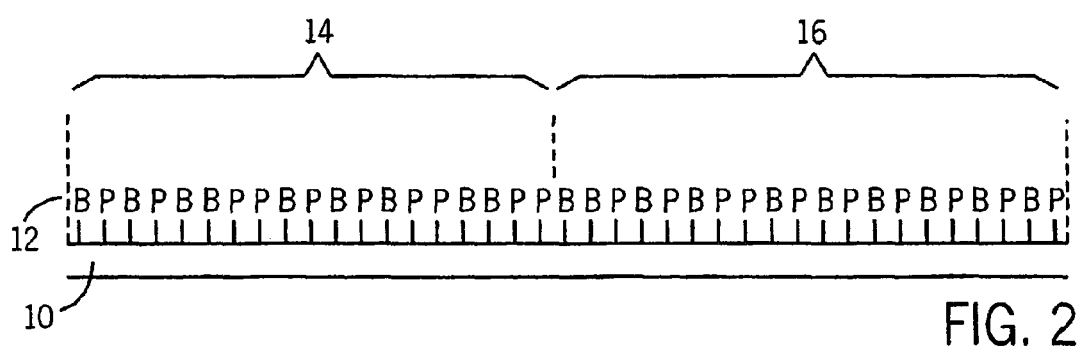
Figure 3:
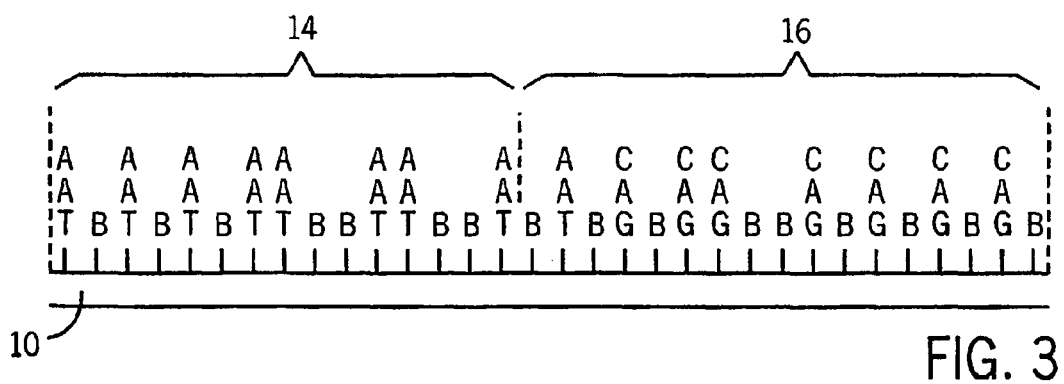
Figure 4:
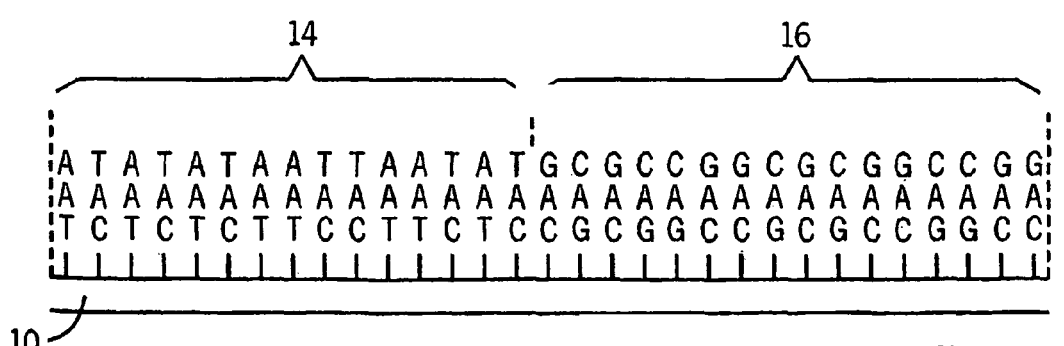

Again, the method by which the construction of multiple probes in single features is enabled is an elegant and relatively simple modification of the existing microarray synthesis methods. First, on the activated substrate, a light directed de-protection step is performed which is limited in time duration. The time is selected to be a selected proportion, such as one-half, of the time which has been found to be necessary to de-protect the entire surface area of the features. We have found that if one-half the minimum exposure time necessary to de-protect the entire feature area is used, approximately one-half of the surface area of each feature area will be de-protected. This concept is illustrated in the schematic of FIG. 1. In FIG. 1, the prepared substrate 10 is coated with reactive groups, such as silanes with reactive hydroxyl groups, to which photo-labile protecting groups "P" have been attached. The layer of photo-labile protecting groups is designated by the reference number 12. This portion of the microarray is intended to encompass two features, here designated 14 and 16. Light, designated at 18, is shined on the entire array for a sufficient period of time to de-protect about one-half of the photo-labile protecting groups "P". The de-protected areas of the features are then capped by a protecting groups that will not be disturbed by the synthesis of the remaining probes, such as adding an acid labile protecting group, designated in FIG. 2 by "B". Thus at this point, about one-half of the area of each feature is protected by a photo-labile protecting group while the other half is protected by an acid labile protecting group. Then a light directed de-protection step is performed to saturation so that the remaining photo-labile protecting groups are all removed from the microarray area. Following that, an otherwise conventional a probe synthesis process is conducted to completion in all the areas which are not capped by the acid-labile blockers. This is illustrated in FIG. 3 where an illustrated three nucleotide probe set TAA has been synthesized in feature 14 while a set of probes of sequence GAC has been synthesized in feature 16. The three nucleotides are illustrative only since, in actual practice, of course, the probes are much longer, typically about 25 nucleotides in length, although they can be constructed to be up to 100 nucleotides with reasonable accuracy. After the synthesis of this first set of oligonucleotide probes is complete, the synthesized probes are capped by a capping agent that is neither light nor acid labile. Then an acid is used to remove the acid labile protecting groups "B" from the substrate to expose the areas of the microarray in which no probes have yet been synthesized. Then another set of probes are synthesized on the microarray in exactly the same fashion as before, except that the sequence of the synthesize probes may now be different. Simply for purposes of illustration, in the trivial example in the illustrations in FIG. 4, a second probe of sequence CAT has been constructed in feature 14 while a second probe set of sequence CAG has been constructed in feature 16. In actual practice, synthesizing two probes sets in each feature by the method described here has turned out to be practical and readily achievable. The relative amounts of the first and second probe sets can even be adjusted simply by modifying the time of the partial light directed de-protection step at the start of the process.

Note that the direction of probe synthesis depends solely on the nature of the nucleotides uses. When nucleotides are added to the building probes set, the added nucleotides are added with a photo-labile protecting group already attached to them. The direction of probe synthesis, i.e. whether the probes are synthesized 3' to 5' or 5' to 3', is determined solely by whether the added nucleotide has the photo-labile protecting group attached to its 3' or 5' end. Since nucleotides with suitable photo-labile protecting groups, including NPPOC, which is the) preferred reagent for use herein, are available with the NPPOC attached at either the 3' or 5' end of the nucleotide, it is readily possible to synthesize probes in either selected orientation. In fact, the direction of one set of probes in a given feature does not have to match the direction of the other set of probes in the same feature. We have made microarrays in which 3' to 5' and 5' to 3' probes are synthesized in the same feature areas of the microarrays.

It is recognized that many different compounds may be used as binding compounds or protecting groups during the synthesis of microarrays. Although reference is made below to specific compounds used during the synthesis process, one of ordinary skill in the art would recognize that other binding compounds and protecting groups could also be used in the practice of the present invention. The below examples merely serve as a discussion of one embodiment of the present invention and is in no way intended to limit its scope.

The present invention allows for two or more different oligonucleotides to be built in a single feature area. To produce two oligonucleotides per feature area, one layer of a base associated with a photosensitive protective group, such as NPPOC protected bases, is coupled to the array surface. The base is then partially deprotected with an appropriate light source. The amount of light dosed on the array will have the effect of removing the photosensitive protective group from only a percentage of the feature area, thus controlling the ratio of the different oligonucleotides synthesized. When the desired percentage of the original base is removed, a second base carrying a protecting group that is not sensitive to the light being employed, such as acid labile di-methoxy-trityl (DMT), is coupled to the free hydroxyls on the surface of the deprotected portion of the feature area. Once coupled, the remaining photosensitive protective groups are removed by dosing the feature area with more of the light source. The hydroxyl groups that are freed by the second dose of light (and thus not protected by DMT) are thus free to be used to synthesize light directed DNA probes in the normal fashion. In absence of any highly acidic compounds, such as trichloroacetic acid (TCA), the DMT protected sites within each feature will be unaffected and saved for future use in building a second group of DNA strands.

After the first group of DNA strands is synthesized, the DNA is capped with a capping compound, such as acetic anhydride and tetrahydrofuran, to inhibit further strand building, and the synthesis of the second group of DNA strands is begun. First, the DMT protective group is removed from the original deprotected group by exposure to a compound effective in removing DMT, such as the highly acidic compound TCA. Once the DMT is removed, the second group of DNA strands is synthesized in the normal fashion. Upon completion, the array is placed in a deprotection solution to remove the base protecting groups and the cap placed on the first set of DNA strands, resulting in an array with two different oligonucleotide strands per feature.

It is envisioned that even more than two species of probes can be constructed in a common feature of a microarray. To increase the number of different oligonucleotides that are present in one feature, several rounds of partial deprotection by light, intermixed by coupling with different types of protecting groups may be employed. Each of these protecting groups must be able to be independently removed from the surface. When each type of group is removed, DNA strands are built at those locations. For example, after deprotection of 33% of the sites with light, a DMT group may be used as a protecting compound. After deprotection of a second 33% of the sites with light, a base labile FMOC group may be added as a second protecting compound. The remaining groups may then be removed with light, and a first group of DNA strands built and capped. TCA may then be used to remove the DMT group, allowing a second group of DNA strands to be built and capped. Finally, FMOC may be removed using a weak base, allowing for a third group of DNA strands to be built and capped.

It is envisioned that other types of protecting groups could also be used, thus allowing for the application of different chemical treatments or different wavelengths of light. The direction of synthetic DNA may also be controlled using either 5' amidites or 3' amidites for synthesis of a given strand. It is also possible to mix 5' and 3' amidites within one strand. Microarrays can be constructed in which all the features have more than one probe in them, or the microarray can have some features with a single probe and some features with multiple probes in them. This techniques permits the microarray to be highly customized to particular unique applications.

Figure 5:
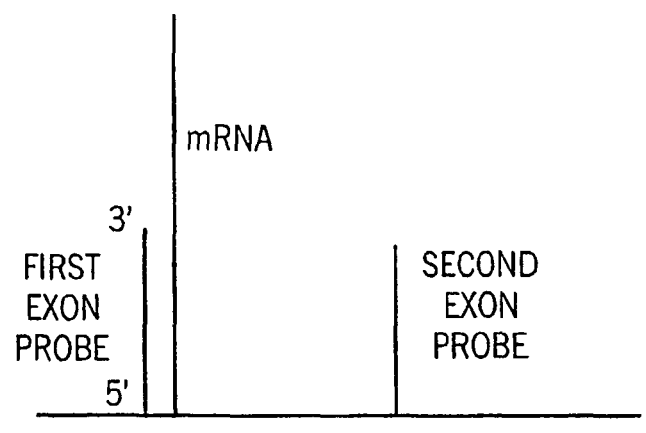
FIG. 5 is an illustration of a type of assay that is made possible, for the first time, from the fact that the microarray has two oligonucleotides in each feature.
Figure 5:
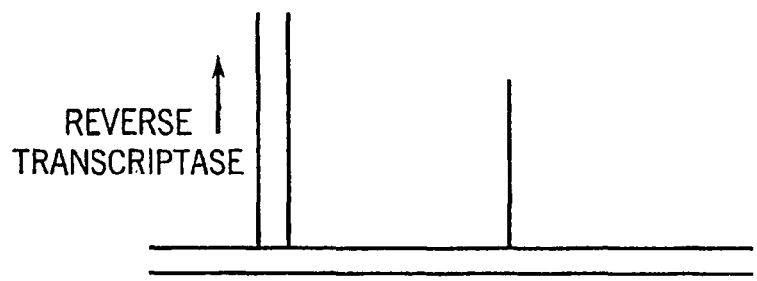
Figure 5:
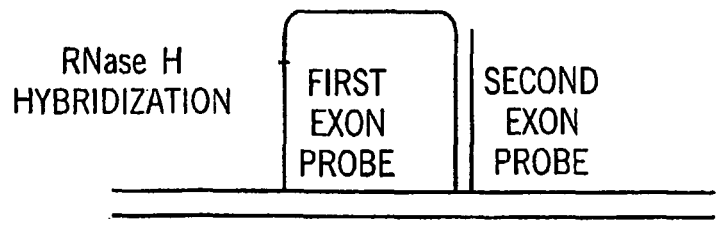
Figure 5:
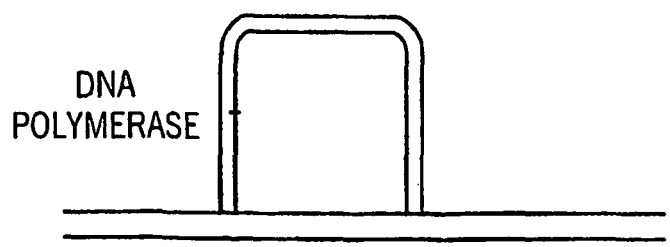
Figure 5:
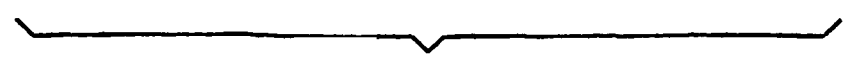

The ability to make microarrays with more than one oligonucleotide in a feature broadens the range of analyses that can be conducted with microarrays. For example, one interesting application enable by this approach is the design of microarrays intended to permit studies of transcript splicing in the expression of eukaryotic genes. It is believed, for example, that the number of genes in the human genome may be insufficient to explain all the proteins in the human body, and that intermediate mRNA splicing may explain some of the diversity in proteins. This phenomenon is difficult to study using conventional microarrays. Illustrated in FIG. 5 is a method for using microarrays with two probes in a feature to study mRNA splicing. The two probes constructed in this illustrative feature are designed to detect whether a covalent linkage between two exons of a gene occurs in a given mRNA sample, i.e. to see if an mRNA exists in a cell of tissue which includes both exons. One of the set or probes in the feature is designed to be complementary to the mRNA of a particular first target exon of the gene being studied. The mRNA is hybridized to the microarray, and the mRNA species hybridizes to the first set of probes only if the target exon is in the mRNA species. This is illustrated at step 20 in FIG. 5. The mRNA binds only to the probe for the first exon since the probes for the second exon are of the opposite sense as the probes for the first exon. Then, reverse transcriptase is used to extend the probe oligonucleotide, using the bound mRNA as a template, as illustrated at 22 in FIG. 5. The first exon is covalently extend to be a longer piece of DNA complementary in sequence to the mRNA, like a cDNA. The mRNA is then removed from the micoarray, for example using RNase H to digest the mRNA away, leaving only the extended probe. Then another hybridization step is performed, and, as indicated at 24 in FIG. 5, the distant end of the extended first probe will hybridize to the second probe only if the second probe set is complementary to far end of the extended first probe. The second probe set is thus designed to be complementary to the DNA (not the mRNA) of another target exon in the gene being studied. Then a DNA extension reaction is performed, with a DNA polymerase, such as DNA polymerase I, to add nucleotides to the single stranded part of the complex, beginning at the terminus of the second probe. The DNA extension reaction will only occur if the hybridization to the second set of probes occurred. By incorporating fluorescently labeled nucleotides in the DNA extension step, indicated at 26 in FIG. 5, the completed double stranded DNA molecule can be made fluorescent, or detectable in any other convenient manner. When the microarray is read, only features which bound to mRNA which contained sequences complementary to both of the DNA probes in that feature will fluoresce. With a set of several features designed to test the various exons in a gene, the entire gene splicing pattern in a cell or tissue can be determined. Thus it can be determined which exons are linked by common transcripts in given cells, and information about gene splicing can be revealed using microarrays.

EXAMPLES

Example 1

Using the methods described above and a maskless array synthesizer instrument, two oligonucleotides were synthesized in the same feature area using the method of the present invention, with the ratio of one oligonucleotide to the other varied horizontally across the array. The array was then hybridized with two oligonucleotides that were complementary to the array oligonucleotides. One of these oligonucleotides was labeled with Cy3, the other with Cy5. The resulting scan of the hybridized microarray to test samples revealed that the Cy3 oligo has increasing surface density from left to right, while the Cy5 oligo is increasing in density from right to left. The result were readily apparent in fluorescent imaging.

Example 2

An array was designed having six 10×10 feature sections, with different oligonucleotides synthesized in common features of the array. Three different oligonucleotides were combined in all possible permutations in the array with each of the other oligonucleotides. Test samples of known sequence were then hybridized to the microarray thus made. Each sample hybridized only the specific area in which probes complementary to that sample had been synthesized.

We claim:

1. A method for synthesizing different oligonucleotides in the same feature on a substrate for a microarray, the method comprising the steps of:

providing the substrate for manufacturing the microarray, the substrate having a plurality features comprising photo-labile first protecting groups formed on its surface, exposing at least one feature to light for a period of time sufficient to cleave only a portion of the photo-labile first protecting groups to leave a first unprotected area of the at least one feature; coupling a non-photosensitive second protecting group to the first unprotected area;

further exposing the at least one feature to light for a period of time to cleave the photo-labile first protecting groups from the at least one feature to leave a second unprotected area of the at least one feature;

building a first group of oligonucleotides in the second unprotected area using an amidite having a protecting group at its 5' position; capping the first group of oligonucleotides with a capping compound that is not photolabile; removing the second protecting group from the at least one feature to unprotect the first area; and building a second group of oligonucleotides in the first unprotected area using an amidite having a protecting group at its 3' position, such that the at least one feature comprises both 3'-5'-oriented oligonucleotides and 5'-3'-oriented oligonucleotides attached to the substrate surface.

2. The method of claim 1 wherein the period of time is sufficient to cleave about 50% of the photo-labile protecting groups.

3. The method of claim 1 wherin the period of time is sufficient to cleave about 33% of the photo-labile protecting groups.

4. The method of claim 1 wherein the second protecting group is acid labile.

5. The method of claim 4 wherein the second protecting group is di-methoxy-trityl.

6. The method of claim 4 wherein the capping compound is acetic anhydride and tetrahydrofuran.

* * * * *